US009110031B2

(12) United States Patent
Counord et al.

(10) Patent No.: US 9,110,031 B2
(45) Date of Patent: Aug. 18, 2015

(54) DEVICE AND METHOD INTENDED TO MEASURE THE PROPERTIES OF A COMPLEX MEDIUM BY ANALYSIS OF THE VARIATION IN BACKSCATTERED AND/OR TRANSMITTED LIGHT

(75) Inventors: Jean-Louis Counord, Rueil-Malmaison (FR); Jacques Dufaux, Sainte Genevieve des Bois (FR)

(73) Assignee: CENTRE NATIONAL DE LA RECHERCHE SCIENTIFIQUE-CNRS, Paris (FR)

( * ) Notice: Subject to any disclaimer, the term of this patent is extended or adjusted under 35 U.S.C. 154(b) by 0 days.

(21) Appl. No.: 13/703,136

(22) PCT Filed: Jun. 7, 2011

(86) PCT No.: PCT/FR2011/051293
§ 371 (c)(1),
(2), (4) Date: Dec. 10, 2012

(87) PCT Pub. No.: WO2011/154655
PCT Pub. Date: Dec. 15, 2011

(65) Prior Publication Data
US 2013/0100435 A1 Apr. 25, 2013

(30) Foreign Application Priority Data

Jun. 9, 2010 (FR) ...................................... 10 54556

(51) Int. Cl.
*G01N 33/48* (2006.01)
*G01N 21/84* (2006.01)
(Continued)

(52) U.S. Cl.
CPC ............ *G01N 21/84* (2013.01); *B01F 11/0028* (2013.01); *B01F 2215/0037* (2013.01); *G01N 2021/513* (2013.01)

(58) Field of Classification Search
CPC .......... G01N 33/48; G01N 21/59; G06F 7/00; G06F 17/30; G06K 7/10
USPC ...................... 356/39, 427; 235/470; 700/216
See application file for complete search history.

(56) References Cited

U.S. PATENT DOCUMENTS

| 4,964,728 A * | 10/1990 | Kloth et al. ................... 356/427 |
| 2002/0100806 A1 * | 8/2002 | Harrop .......................... 235/470 |

(Continued)

FOREIGN PATENT DOCUMENTS

| DE | 201 12 276 | 9/2001 |
| FR | 2 383 444 | 10/1978 |

(Continued)

OTHER PUBLICATIONS

International Search Report dated Mar. 8, 2012, corresponding to PCT/FR2011/051293.

(Continued)

*Primary Examiner* — Tarifur Chowdhury
*Assistant Examiner* — Jamil Ahmed
(74) *Attorney, Agent, or Firm* — Young & Thompson

(57) ABSTRACT

Disclosed is a device and method intended to measure the properties of a complex medium (2) by analyzing the variation in light backscattered by this complex medium (2) after a prior stirring step. The device and the method include movement element (14) capable of subjecting the receiving element (6) to a stirring movement including at least a back-and-forth movement along a directional vector extending by a not insignificant amount along the longitudinal direction, so as to generate shear stresses in the complex medium (2), thereby destroying aggregates in the complex medium (2) when a container (4) is received and supported by the receiving element (6).

25 Claims, 5 Drawing Sheets

(51) Int. Cl.
    *B01F 11/00* (2006.01)
    *G01N 21/51* (2006.01)

(56) References Cited

U.S. PATENT DOCUMENTS

| | | | |
|---|---|---|---|
| 2007/0064521 A1 | 3/2007 | Miszenti | |
| 2010/0198392 A1* | 8/2010 | Eliuk et al. | 700/216 |

FOREIGN PATENT DOCUMENTS

| | | | |
|---|---|---|---|
| FR | 2 501 057 | | 9/1982 |
| GB | 2295892 A | | 12/1996 |
| JP | 08160031 A | | 6/1996 |
| JP | 09508315 A | | 8/1997 |
| JP | 2001149800 A | | 6/2001 |
| JP | 2002082118 A | | 3/2002 |
| JP | 2007155509 A | | 6/2007 |
| JP | 2008298692 A | | 12/2008 |
| WO | 9521015 A1 | | 8/1995 |
| WO | 2008/072870 | | 6/2008 |

OTHER PUBLICATIONS

Japanese Office Action dated Jan. 27, 2015, for corresponding patent application.

* cited by examiner

DEVICE AND METHOD INTENDED TO MEASURE THE PROPERTIES OF A COMPLEX MEDIUM BY ANALYSIS OF THE VARIATION IN BACKSCATTERED AND/OR TRANSMITTED LIGHT

BACKGROUND OF THE INVENTION

The invention relates to the field of measuring the properties of a complex medium.

The invention relates to a device and a process designed to measure the properties of a complex medium by an analysis of the variation in light that is backscattered and/or transmitted by this complex medium after a preliminary stirring stage.

SUMMARY OF THE INVENTION

By way of nonlimiting example, such a device is used for measuring an aggregation time and/or a sedimentation index of a complex medium, such as a blood suspension.

For example, the analysis of the rate of aggregation of a blood suspension makes it possible to identify the elevation of the aggregation of blood in patients suffering from pathologies such as diabetes, hypertension, cerebrovascular accidents, venous return stasis, glaucoma, etc.

Actually, the viscosity of the blood depends on numerous parameters, including the aggregability of the red globules as well as the composition of macromolecules of plasma. The aggregability of the red globules, which is a reversible phenomenon, depends on the flow conditions. The size of the aggregates that are formed can reach 50 to 100 µm in the low shear zones of the microcirculatory network. In these zones, more particularly on the venular side, the aggregates cluster in the center of the vessel, creating, near the wall, a layer of plasma that is devoid of globules; this promotes a reduction of the apparent viscosity of the blood suspension. This reduction can be performed, however, only if the aggregation level is not too high and the aggregates can be destroyed in the passage of the terminal capillaries with a diameter that is smaller than the size of the aggregate, where the shearing increases. In contrast, when the aggregation is too high, the circulation is slowed down and even blocked. The knowledge of aggregation in the blood is therefore useful for the physician seeking to prevent certain hemorheological risks.

According to a first of its aspects, the invention relates to a device that is designed to measure the properties of a complex medium by an analysis of the variation in the light that is backscattered and/or transmitted by the complex medium during a measuring phase after a preliminary stirring stage, with this complex medium comprising aggregates and being contained in a container extending in a longitudinal direction. In this connection, the measuring device comprises receiving means that are capable of accommodating and supporting the container; holding means that are capable of holding this container in a stationary or essentially stationary position with respect to the receiving means when these receiving means are driven by a stirring motion that causes the destruction of the aggregates of said complex medium; means for support of a module for measuring the light that is backscattered and/or transmitted by said complex medium, with the support means being capable of being combined structurally with the measuring module in such a way as to support it and arranged with respect to said receiving means in such a way as to make it possible for the measuring module to emit emission light rays in such a way as to illuminate said complex medium and to receive light rays that are backscattered and/or transmitted by said complex medium at any moment of the measuring phase when this measuring module is structurally combined with the support means.

Such a device is known from the state of the art, in particular by the example given by the document "*RBC Laser Diffractometry and RBC Aggregation with a Rotational Viscometer: Comparison with Rheoscope and Myrenne Aggrometer*," M. R. Hardeman, R. M. Bauersachs, H. J. Meiselman. Clin. Hemorheol. Actually, this document describes a device based on the measurement of the light that is backscattered by the complex medium that constitutes the blood suspension.

Its principle is as follows. The blood suspension is illuminated by a light beam in such a way that the more aggregated the red globules, the lower the backscattered light intensity, with the illuminated surface being smaller. The blood suspension—constituting the complex medium—is placed between two coaxial cylinders, one of which can rotate quickly so as to subject the aggregates to a shear that is sufficient for disaggregating them. When the rotating cylinder is suddenly stopped, the aggregates get back together again more or less quickly. The aggregation time is then one of the parameters making it possible to characterize the aggregation capacity of the red globules from the analysis of curves showing the temporal variation in the intensity of the light that is backscattered by the complex medium.

However, the use of this device presents several drawbacks. Firstly, it is necessary, to carry out the measuring, to open the tubes that contain blood samples so as to introduce the blood suspension between the two coaxial cylinders. However, the legislation set in place in recent years relating to the handling of human blood imposed numerous precautions, making this type of handling unworkable. In addition, the cleaning of the thin space between the two coaxial cylinders is particularly difficult and requires a preparation time of approximately 15 minutes per sample. Likewise, the time advised for carrying out the disaggregation of the aggregates for taking the measurement is several minutes, which is prohibitive for routine measurements. Finally, the complex mechanical system that consists in rotating one of the coaxial cylinders relative to the other is of relatively high cost.

Also known from the state of the art is the document WO-A-2008/072870 that describes a device for measuring the rate of aggregation of a blood suspension. This device comprises in particular a container for accommodating the blood suspension and a stirring mechanism to be integrated into the container for disaggregating the aggregations contained in this blood suspension in such a way as to obtain the initial conditions of the measurement as well as an induction unit that makes it possible to put the stifling mechanism into motion.

As above, this device has several drawbacks. Actually, the dimensions of the container necessarily have to be suitable for accommodating a stirring mechanism, which generally involves transferring the blood suspension from a blood sample tube to a special container. In addition, it is essential to introduce the stifling mechanism inside the container, which causes restrictive safety problems taking into account abovementioned legislative standards with respect to the handling of blood samples. It should also be emphasized that the disaggregation achieved using the stirring mechanism is not optimal.

In a field that is different from that of the stifling mechanisms designed to mix blood with an anti-coagulating liquid, the document FR-A-2 501 057 is also known. The latter has a mechanism for stirring blood in pouches having an oscillating plate whose motion is imparted by three rollers forming an inclined plane. Three roller-support arms are attached to a turntable comprising a gearwheel that engages a pinion attached to the output shaft of a speed reducer driven by an electric motor.

Again, this device has drawbacks. It does not make it possible to stir the pouch enough to achieve disaggregation of the aggregates contained in the blood. Also, in any case, the stirring should be extended for a significant period that is not suitable for routine measurements.

In this context, the invention has as its object to propose a device and a process that are designed to measure the properties of a complex medium that is free of at least one of the above-mentioned limitations.

More particularly, there is an unsatisfied need for a device and a process designed to measure the properties of a complex medium by an analysis of the variation in the light that is backscattered and/or transmitted by the complex medium during a measuring phase after a preliminary stirring stage that makes it possible to carry out an optimum disaggregation of the aggregates in a minimum time interval, without requiring the opening of the container receiving the complex medium that is to be analyzed.

For this purpose, the device and the process according to the invention, furthermore in accordance with the generic definition that the preamble above provides, are essentially characterized in that they comprise means for putting into motion that are capable of imposing on said receiving means a stirring motion comprising at least one back-and-forth movement according to a directional vector extending in a significant proportion in the longitudinal direction in such a way as to cause shear stresses in the complex medium bringing about the destruction of the aggregates of said complex medium when said container is accommodated and supported by the receiving means.

Owing to this arrangement, it is possible to impose on a container, such as a blood sample tube, a motion that can produce shear stresses that are high enough to disaggregate the aggregates contained in the complex medium within a limited time interval. Surprisingly enough, it was actually noted that this motion—similar to the gesture by a nurse who stirs a blood sample tube essentially over its length—makes it possible to obtain a particularly high disaggregation rate in a short time. In addition, such a configuration makes it possible to use a blood suspension that is taken directly from a patient without the necessity for transfusing this blood suspension from the blood sample tube to a container that is specially provided for this purpose. In particular, the stage for cleaning the container is also eliminated, and, after analysis, the sample tube can be reused without the state of the blood suspension having been modified.

It should be noted that a "directional vector extending in a significant proportion in the longitudinal direction" means any directional vector that has a longitudinal component—corresponding to a projection of the directional vector in the longitudinal direction of the container when it is in position in the receiving means—sufficient for disaggregating the aggregates of the complex medium. Preferably, this longitudinal component exceeds any other transverse component extending in a direction that is perpendicular to the above-mentioned longitudinal direction.

It should also be noted that the term of "complex medium" indicates any type of medium that, when it is subjected to shear stresses, changes structure, which brings about the destruction of aggregates or other types of clusters and allows a return to a reproducible initial state.

According to one embodiment, the means for putting into motion are capable of imposing on said receiving means a stirring motion that comprises at least one back-and-forth movement according to a unidirectional translational movement.

According to one embodiment, the means for putting into motion are capable of imposing on said receiving means a stirring motion that comprises at least one back-and-forth movement according to a circular translational movement around an axis of rotation.

According to one embodiment, the means for putting into motion are capable of imposing on said receiving means a stirring motion that comprises at least one back-and-forth movement in a rotation around an axis of rotation. In particular, the axis of rotation can be positioned at a distance that is essentially between 50 and 200 millimeters from the center of gravity of the receiving means, and the back-and-forth movement around the axis of rotation can be essentially between 10° and 90°.

It was noted that such rotational motion is sufficient to bring about very simply high shear stresses inside the container and thus to obtain a high disaggregation rate.

According to one embodiment, the means for putting into motion comprise a motor that has a rotary shaft, a lever arm working with the rotary shaft and connected to the receiving means in such a way that the means for putting into motion are capable of driving the receiving means in movement around the rotary shaft.

According to one embodiment, the holding means are formed by O-ring seals that cover a portion of the inside surface of the receiving means. Thus, the container can be held with receiving means by simple adhesion with the O-ring seals.

According to one embodiment, the holding means are formed by a clamp or a stop part that may or may not be deformable.

According to one embodiment that comprises the module for measuring the light that is backscattered and/or transmitted by said complex medium, the latter comprises a light source that is capable of emitting the emission light rays in the direction of said complex medium in such a way as to illuminate said complex medium, and an optical detector that is capable of receiving the light rays that are backscattered and/or transmitted by said complex medium in response to the illumination of said complex medium.

According to one embodiment, the light source emits monochromatic radiation.

According to one embodiment, the support means of the measuring module are structurally and functionally combined with receiving means of the container in such a way that the stifling motion imposed on the receiving means is also imposed on the measuring module. Cohesion between the measuring module and the receiving means is thus obtained, which makes it possible to ensure the relative position of the measuring module relative to the complex medium contained in the container.

According to one embodiment, the support means of the measuring module are structurally separated from the receiving means in such a way that these support means are in relative motion with respect to these receiving means when said receiving means are in a stirring motion.

According to one embodiment, the receiving means have a window that is arranged relative to the support means in such a way that the emission light rays and the backscattered light rays are able to pass through this window during the measuring phase.

According to another aspect, the invention also relates to a process that is designed to measure the properties of a complex medium by an analysis of the variation in the light that is backscattered and/or transmitted by the complex medium during a measuring phase after a preliminary stifling stage, with this complex medium comprising aggregates and being contained in a container extending in a longitudinal direction, with the process comprising a large number of successive stages, during which:

The container is accommodated and supported by receiving means;

The container is held in a stationary or essentially stationary position with respect to the receiving means;

With the measuring phase consisting in emitting emission light rays in such a way as to illuminate the complex medium and to receive light rays that are backscattered and/or transmitted by said complex medium.

More particularly, according to the invention, the preliminary stirring stage of the container consists in:

Putting the receiving means into a stirring motion comprising at least one back-and-forth movement according to a directional vector extending in a significant proportion in the longitudinal direction, In such a way as to cause shear stresses in the complex medium bringing about the destruction of the aggregates of said complex medium when said container is accommodated and supported by the receiving means.

According to one embodiment, the preliminary stifling stage consists in putting the receiving means and the container into a stirring motion comprising at least one back-and-forth movement according to a unidirectional translational movement.

According to one embodiment, the preliminary stifling stage consists in putting the receiving means and the container into a stirring motion comprising at least one back-and-forth movement according to a circular translational movement around an axis of rotation.

According to one embodiment, the preliminary stifling stage consists in putting the receiving means and the container into a stirring motion that comprises at least one back-and-forth movement in a rotation around an axis of rotation.

According to one embodiment, the axis of rotation is positioned at a distance that is essentially between 50 and 200 millimeters from the center of gravity of the receiving means.

According to one embodiment, the back-and-forth movement around the axis of rotation is essentially between 10° and 90°.

According to one embodiment, the container is held by an O-ring seal that covers a portion of the inside surface of the receiving means.

According to one embodiment, the container is held by a clamp or a stop part that may or may not be deformable.

According to one embodiment, during the measuring phase, a light source emits the emission light rays in the direction of said complex medium in such a way as to illuminate said complex medium; an optical detector receives the light rays that are backscattered and/or transmitted by said complex medium in response to the illumination of said complex medium.

According to one embodiment, the light source emits monochromatic radiation.

According to one embodiment, the support means of the measuring module are combined structurally and functionally with the receiving means of the container in such a way that the stirring motion imposed on the receiving means is also imposed on the measuring module.

According to one embodiment, the support means of the measuring module are separated structurally from the receiving means in such a way that these support means are in relative motion with respect to these receiving means when said receiving means are in a stirring motion.

According to one embodiment, the receiving means have a transparent window with respect to the support means of the measuring module in such a way that the emission light rays and the backscattered light rays pass through this window during the measuring phase.

According to one embodiment, the measuring module transmits data collected during the measuring phase to an analysis unit that may or may not have been structurally separate.

According to one embodiment, the analysis unit uses the collected data for calculating the rate of sedimentation of said complex medium after the measuring phase.

BRIEF DESCRIPTION OF THE DRAWING FIGURES

Other characteristics and advantages of the invention will emerge clearly from the detailed description that is given below by way of indication and is in no way limiting, with reference to the accompanying drawings, in which.

Figure 5A:
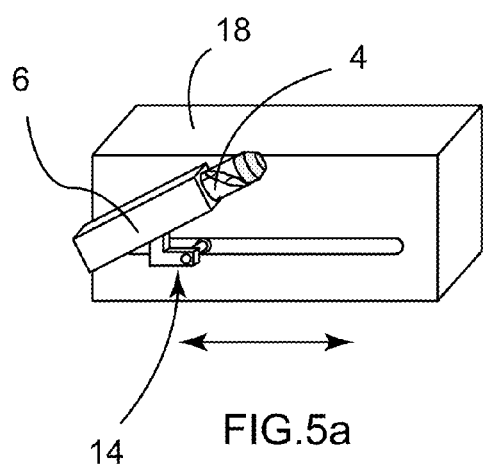
Figure 5B:
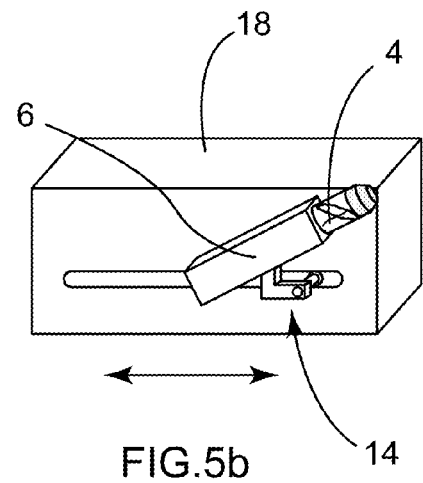
Figure 6A:
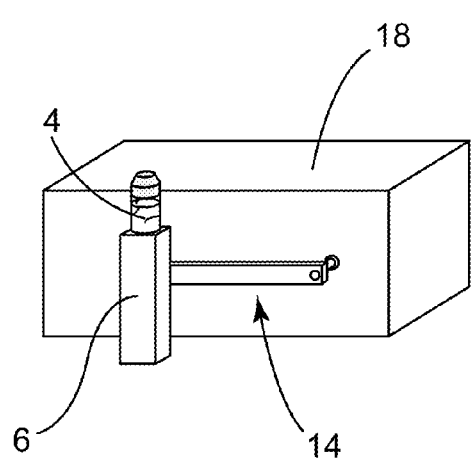
Figure 6B:
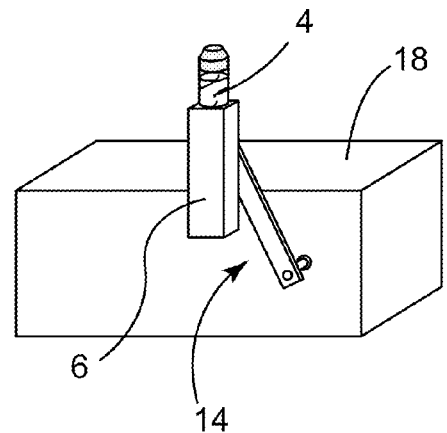

FIGS. 5a and 5b show a diagrammatic view of another embodiment of the device according to the invention in which the stifling motion corresponds to a movement according to a unidirectional translational movement; and FIGS. 6a and 6b show a diagrammatic view of another embodiment of the device according to the invention in which the stifling motion corresponds to a movement according to a circular translational movement around an axis of rotation.

DETAILED DESCRIPTION OF THE INVENTION

Figure 1:
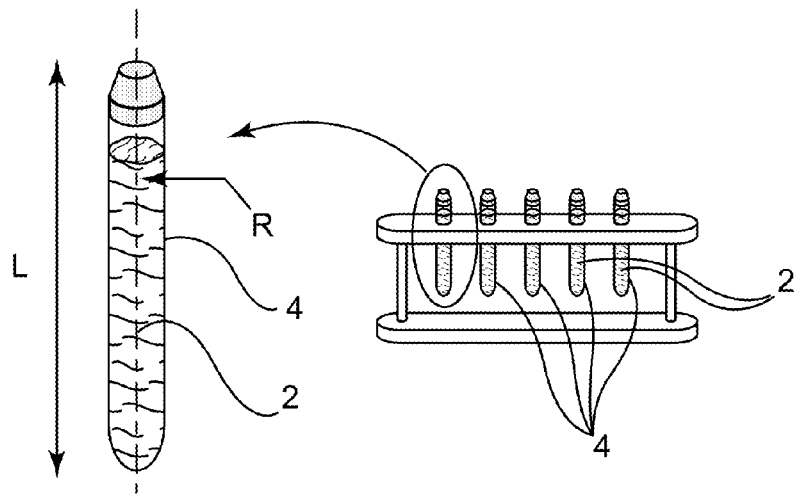
FIG. 1 shows a perspective view of a device designed to measure the rate of aggregation of a blood suspension contained in a blood sample tube by an analysis of the variation in the light that is backscattered by the blood suspension during a measuring phase after a preliminary stirring stage.
Figure 1:
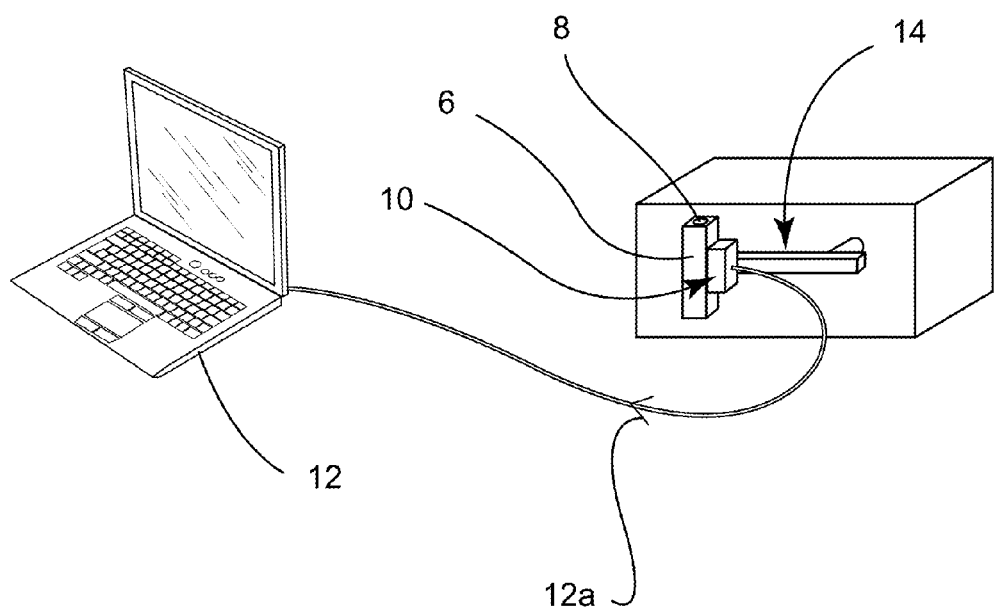

FIG. 1 shows, in perspective, a sample embodiment of a device according to the invention that is designed to measure the rate of aggregation of a blood suspension 2 drawn off from a patient from a sample tube 4. The blood suspension 2 is therefore in the sample tube 4, and the measurement can advantageously be taken directly from this sample tube 4.

Thus, the measurement can be taken directly in the patient's bed after having carried out the sampling. In addition, it is not necessary to initiate any transfer of the blood suspension 2 from the sample tube 4 and to a specific container. The risks of contamination of the medical personnel are therefore limited.

It should be noted that the sample tube 4, as is the standard today, has an essentially cylindrical shape that extends in a longitudinal direction. The sample tube 4 therefore has an essentially circular cross-section, with a radius R, as well as a length L in the longitudinal direction.

This sample tube 4 could be replaced by any other type of container that is analogous or similar provided that it is at least partly transparent and capable of accommodating a complex medium and that has a shape that extends essentially in a longitudinal direction.

In the same way, within the framework of this sample embodiment, the complex medium is formed by a blood suspension 2. However, it could also be considered to take a measurement on a complex medium that is different since the latter is likewise to move from a first aggregation state to a second aggregation state during a preliminary stifling stage as described below.

For the purpose of measuring the aggregation time, the device has as its object to analyze the variation in the light that is backscattered by the blood suspension 2 immediately after a preliminary stifling stage.

To do this, the device comprises a module 6 on the inside of which is defined a chamber 8 into which the sample tube 4 can be inserted. This chamber 8 is also essentially cylindrical and has a circular cross-section with a radius that is slightly greater than the radius R of the cross-section of the sample tube 4. Consequently, the chamber 8 makes it possible to accommodate and to support the sample tube 4.

According to an advantageous embodiment, the inside surface of the chamber 8 is covered at least partially by an O-ring seal 8a or else a rubbery portion (not shown) that has as its function to hold the sample tube 4 inside the chamber 8 and in a position that is stationary or essentially stationary with respect to this chamber 8 when the module 6 is driven by a stirring motion. More particularly, the geometry of the chamber 8 whose radius is adjusted to the radius R of the sample tube 4 and the simultaneous use of a rubbery portion makes it possible to hold the sample tube 4 in position.

It should be pointed out, however, that the rubbery portion could be replaced by other analogous or similar holding means. More particularly, the rubbery portion could be replaced by a pressure screw that is capable of compressing the sample tube 4 inside the chamber 8 or else by an outside part that is likely to come to rest on the exposed end of the sample tube 4. This rubbery portion could alternatively be replaced by any other analogous or similar mechanical means.

The device of FIG. 1 also comprises support means (not shown) of a module 10 for measuring the light that is backscattered by the blood suspension 2. The measuring module 10 is connected in such a way as to transmit measuring signals to a calculating station 12, making it possible to determine, from the measuring signals 12a emitted by this measuring module 10, the rate of aggregation of the blood suspension 2.

The device also comprises means 14 for putting into motion that are capable of imposing on the module 6 a stirring motion comprising at least one back-and-forth movement according to a directional vector. According to the invention, this directional vector extends in a significant proportion in the longitudinal direction of the sample tube 4 when it is held in position inside the chamber 8, in such a way as to cause shear stresses in the blood suspension 2 bringing about at least partially the destruction of the aggregates contained in said blood suspension 2. This destruction of the aggregates makes it possible to achieve a reproducible initial state from which the measurements making it possible to determine the properties of the complex medium 2 can be established.

Figure 2:
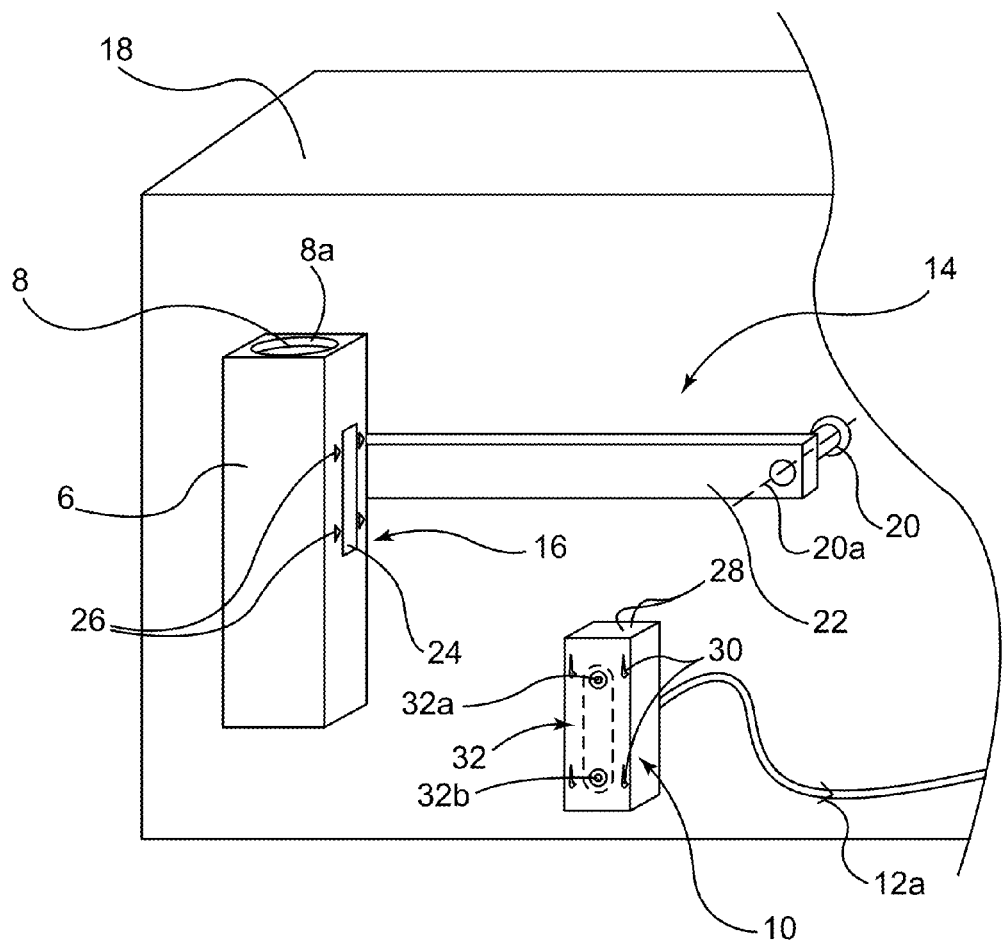
FIG. 2 shows a perspective view of the device of FIG. 1 in which the module for measuring the light is structurally and functionally removed from the receiving means of the blood sample tube.

FIG. 2 shows, in perspective and in a more detailed way, on the one hand, the measuring module 10 and the support means 16 of this measuring module 10, and, on the other hand, the means 14 for putting the device of FIG. 1 into motion.

In the first place, it should be noted that a portion of the means 14 for putting into motion are integrated inside a container 18. This container 18 comprises a motor (not shown) at adjustable speed. According to different embodiments, this motor can have any rotational speed of between 200 and 300 rpm. The motor is connected structurally and functionally to an output shaft 20 by means of a mechanical system—connecting rod/crank, gears, or the like. This mechanical system thus makes it possible to adjust the amplitude and the speed of rotation of the output shaft 20 of which one end is positioned outside of the container 18.

The output shaft 20 is also connected by fixed connection to a support arm 22 that supports, also by a fixed connection, the module 6. The support arm 22 has, according to an advantageous embodiment, a length of 80 millimeters.

Alternatively, but while preserving a limited space requirement, the length of the lever arm could be between 50 and 200 millimeters, and its movement in rotation could be between 10° and 90°.

In contrast, the mechanical system is equipped with a position sensor that is arranged in such a way that the support arm 22 always holds the module 6 in vertical position when the motor is stopped.

Second, it is necessary to note that the sample embodiment of FIG. 2 shows, in a detailed manner, support means 16 of the measuring module 10.

More particularly, according to this embodiment, the module 6 comprises a transparent window 24 that extends essentially in the longitudinal direction of the sample tube 4 as well as four slots 26 that are positioned around the transparent window 24.

Furthermore, the measuring module 10 comprises a body 28 that also extends in a longitudinal direction, four lugs 30 that are capable of working with the slots 26 of the module 6 as well as an optoelectronic unit 32 that comprises an emission light source 32a, such as an infrared-emitting diode with a wavelength of between 800 and 1,000 nanometers, and an optical detector 32b, such as a sensor with integrated amplifying photodiodes of the IPL type (Integrated Photodiode Amplifiers).

According to this embodiment, the light source 32a has a power on the order of several milliwatts.

The four lugs 30 of the measuring module 10 can be engaged in the slots 26 of the module 6 in such a way that the body 28 is held in position relative to the module 6. Thus, the lugs 30 and the slots 26 make it possible to combine the measuring module 10 structurally and functionally with the module 6 in such a way that the stirring motion imposed on the module 6 is also imposed on the measuring module 10. In this assembled position, the emission light source 32a is capable of emitting emission light rays in the direction of the blood suspension 2 in such a way as to illuminate this blood suspension 2 through the transparent window 24 of the module 6. In addition, in this assembled position, the optical detector 32b is capable of receiving the light rays that are backscattered by the blood suspension 2 in response to the illumination by the emission light rays.

Alternatively, the support means of the measuring module 10 could optionally be separated structurally from the module 6 in such a way that the measuring module 10 is in relative motion with respect to the module 6 when said module 6 is in a stirring motion.

For example, the measuring module could be separated structurally from the module 6 but positioned relative to the transparent window 24 in such a way that despite the motion of the module 6 and therefore of the transparent window 24:

Emission light rays emitted by the emission light source 32a can propagate through the transparent window 24 to the blood suspension 2, and Light rays backscattered by the blood suspension 2 can propagate through the transparent window 24 to the optical detector 32b.

Advantageously, the emission light source 32a and the optical detector 32b are placed one above the other and have a predetermined angle of orientation on the order of 30° so that the emission light rays obtained from the emission light source 32a are in large part backscattered to the optical detector 32b.

The bisector of the angle that is defined by this emission light source 32a and this optical detector 32b is preferably positioned at mid-height of the sample tube 4.

The optoelectronic unit 32, and, more particularly, said emission light source 32a and said optical detector 32b are connected by a flexible cable to a power control and power supply box. In contrast, this optoelectronic unit 32 is connected to the calculating station 12 in such a way as to transmit to it the measuring signals 12a collected during the measuring phase.

Figure 3:
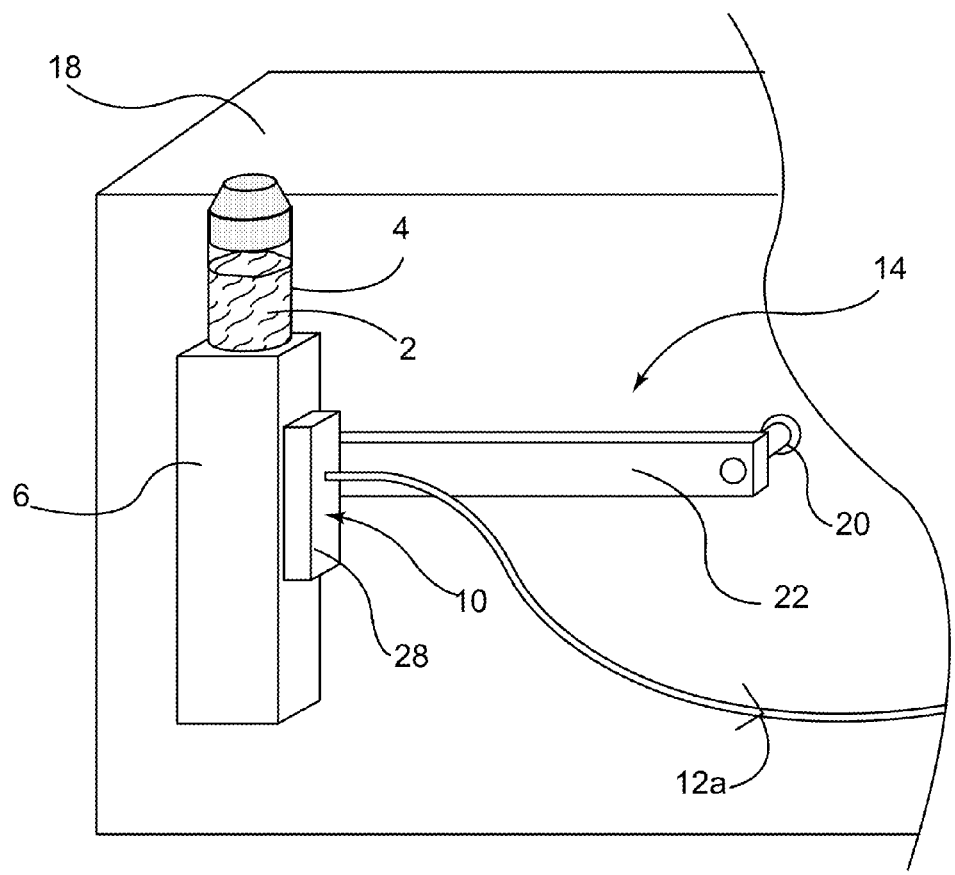
FIG. 3 shows a perspective view of the device of FIG. 1 in which the module for measuring light is structurally and functionally connected to the receiving means of the blood sample tube, and the latter is held in position in the receiving means.

FIG. 3 shows, in perspective and in a detailed manner, the device of FIG. 1 in which the measuring module 10 is structurally combined with the module 6, and the sample tube 4 is inserted into the chamber 8 of the module 6.

Figure 4:
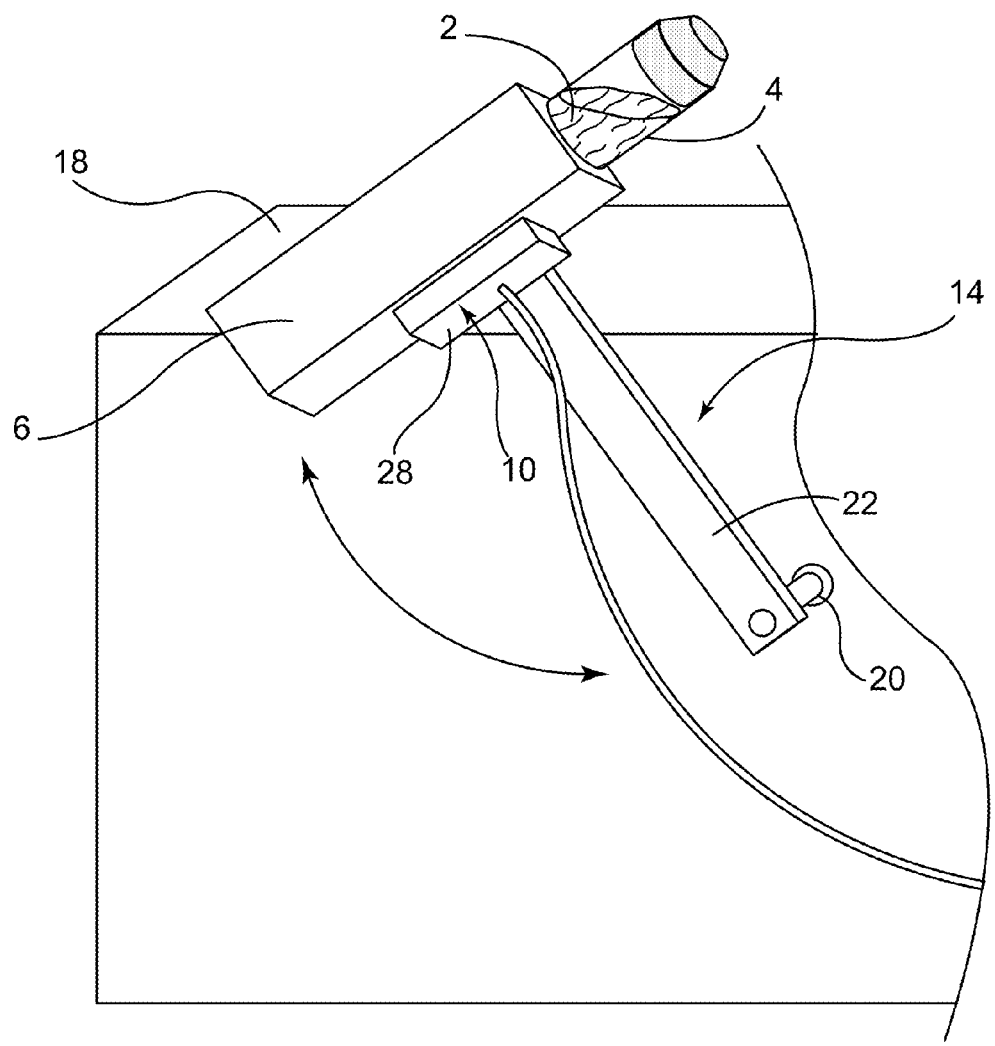
FIG. 4 shows a perspective view of the device of FIG. 3, in which the means for putting into motion move the receiving means of the blood sample tube in a rotation around an axis of rotation.

Several stages used in a sample embodiment of the process according to the invention will now be described based on FIG. 4 that shows, in perspective and in a detailed way, the device of FIG. 1 when the latter is in a stifling motion.

As described above, the process consists in measuring the aggregation time of the blood suspension 2 by an analysis of the variation in the light that is backscattered by this blood suspension during a measuring phase after a preliminary stifling stage.

During this preliminary stifling stage, the sample tube 4 that contains the blood suspension 2 is put into motion. More particularly, the starting of the motor drives the rotation of the output shaft, which makes it possible to pivot the support arm 22 as well as the module 6 around the axis of rotation 20a of the output shaft 20 in a back-and-forth motion.

More particularly, the means 14 for putting into motion impose on the module 6 a back-and-forth movement according to a directional vector that extends in a significant proportion in the longitudinal direction of the sample tube 4 in such a way as to cause shear stresses in the blood suspension 2 that bring about the destruction of the aggregates. This stifling motion advantageously has a stifling frequency of approximately 4 Hz, which makes it possible to impose shear stresses that are high enough to disaggregate the major portion of the aggregates of the blood suspension 2. However, a stirring frequency of between 2 and 6 hertz could also be considered and would make it possible to obtain satisfactory results.

After a preliminary stirring stage of approximately 10 seconds, the motor is stopped.

The measuring module 10 then makes it possible to follow the variation in the light that is backscattered by the blood suspension 2 in a time interval of approximately 2 minutes. The corresponding measuring signals 12a are then transmitted to the calculating station 12 that, by means of a capture card such as a National Instrument DAQPad-12000 and then a data-processing program, makes it possible—by a method that is well known from the state of the art—to deduce the aggregation time of the blood suspension 2.

It should be noted that according to the previously-described embodiment, the means 14 for putting into motion impose a stirring motion that corresponds to a rotation of the module 6 around an axis.

However, as FIGS. 5a, 5b, and 6a, 6b illustrate, other motions comprising at least one back-and-forth movement according to a directional vector that extends in a significant proportion in the longitudinal direction of the sample tube 4 could be used.

More particularly, as FIGS. 5a and 5b illustrate, the device according to the invention, also similar to the embodiment of FIG. 1, could comprise means 14 for putting into motion, making it possible to obtain a stirring motion corresponding to a back-and-forth movement according to a unidirectional translational movement.

This unidirectional translational movement can have a directional vector that extends approximately, but not totally, in the longitudinal direction of the sample tube 4 when the latter is in a position inside the module 6. Thus, it is possible to obtain satisfactory results even if the sample tube 4 is inclined with respect to the direction of translational movement of the means 14 for putting into motion.

Alternatively, and as illustrated in FIGS. 6a and 6b, it would also be possible that the device—also similar to the embodiment of FIG. 1—comprises means 14 for putting into motion making it possible to obtain a stifling motion corresponding to a back-and-forth movement according to a circular translational movement around an axis of rotation 20a.

In practice, it is sufficient that the component of the directional vector in the longitudinal direction, corresponding to the projection of the directional vector in the longitudinal direction of the sample tube 4 when the latter is in position in the module 6, is large enough to disaggregate the aggregates of the blood suspension 2. This longitudinal component can exceed any other transverse component extending in a direction that is perpendicular to the above-mentioned longitudinal direction.

It should be emphasized that the embodiments described above relate to the measurement of the rate of aggregation of a blood suspension 2. However, the device according to the invention is also suitable for taking a measurement of the sedimentation time of the blood suspension 2 or of any other complex medium.

In this respect, the process for measuring the rate of sedimentation differs from the process for measuring the rate of aggregation in that, after the preliminary stifling phase, the analysis of the variation in the light that is backscattered by the blood suspension 2 extends into a time interval of approximately one or two hours and no longer only two minutes. The stages after this preliminary stirring phase—and more particularly the stages for analysis of the light that is backscattered by the complex medium—are well known to one skilled in the art today.

It should also be noted that for taking such a measurement of the rate of sedimentation, it is preferable to use a window that extends essentially over the entire length of the container.

It should also be added that the measuring device according to the invention can, according to an advantageous embodiment, make it possible to measure simultaneously the aggregation time and the rate of sedimentation of the blood suspension 2.

To do this, a first series of emission rays illuminates the blood suspension 2 in a first direction; the aggregation time is then measured by analysis of light rays that are backscattered by the blood suspension 2. In contrast, a second series of emission rays illuminates the blood suspension 2 in a second direction; the sedimentation time is then measured by analysis of the through rays or rays that are backscattered by said blood suspension 2.

The invention claimed is:

1. A device that measures properties of a complex medium, including reversible aggregation phenomenon, by an analysis of the variation in the light that is backscattered and/or transmitted by the complex medium during a measuring phase after a preliminary stirring stage, with this complex medium comprising aggregates and being contained in a container extending in a longitudinal direction, comprising:
   a chamber that is capable of accommodating and supporting the container;
   a holder that is capable of holding the container in a stationary or essentially stationary position with respect to the chamber when the chamber is driven by a stirring motion that causes the destruction of the aggregates of said complex medium;
   a stirring element for putting into motion and imposing on said chamber a stirring motion comprising at least one back-and-forth movement according to a directional vector extending in a significant proportion in the longitudinal direction, with a stirring frequency that causes shear stresses in the complex medium bringing about the destruction of the aggregates of said complex medium when said container is accommodated and supported by the said chamber, said stirring element being located exterior to said holder and said chamber;
   a support for supporting a module for measuring the light that is backscattered and/or transmitted by said complex medium;
   the support being combined structurally with the measuring module, and arranged with respect to said chamber for the measuring module to emit emission light rays to illuminate said complex medium and to receive light rays that are backscattered and/or transmitted by said complex medium at any moment of the measuring phase when this measuring module is structurally combined with the said support,
   wherein the stirring element for putting into motion are capable of imposing on said chamber a stirring motion comprising at least one back-and-forth movement according to a circular translational movement around an axis of rotation, and
   wherein the back-and-forth movement around the axis of rotation is essentially between 10° and 90°.

2. Measuring device according to claim 1, wherein the stirring element for putting into motion is capable of imposing on said chamber a stirring motion comprising at least one back-and-forth movement according to a unidirectional translational movement.

3. Measuring device according to claim 1, wherein the stirring element for putting into motion is capable of imposing on said chamber a stirring motion that comprises at least one back-and-forth movement according to a rotation around an axis of rotation.

4. Device according to claim 1, wherein the axis of rotation is positioned at a distance that is approximately between 50 and 200 millimeters from the center of gravity of the chamber.

5. Measuring device according to claim 1, wherein the stirring element for putting into motion comprise: a motor having a rotary shaft, and a lever arm working with the rotary shaft and connected to the chamber such that the stirring element for putting into motion is capable of driving the chamber in movement around the rotary shaft.

6. Measuring device according to claim 1, wherein the holder is formed by at least one O-ring seal covering a portion of the inside surface of the chamber.

7. Measuring device according to claim 1, wherein the holder is formed by a clamp or a stop part that may or may not be deformable.

8. Measuring device according to claim 1, comprising the module for measuring the light that is backscattered and/or transmitted by said complex medium, and wherein this module for measuring the light comprises:
   a light source that is capable of emitting emission light rays in the direction of said complex medium to illuminate said complex medium,
   an optical detector that is capable of receiving light rays that are backscattered and/or transmitted by said complex medium in response to the illumination of said complex medium.

9. Measuring device according to claim 8, wherein the light source emits monochromatic radiation.

10. Measuring device according to claim 1, wherein the support for the measuring module is combined structurally and functionally with the chamber of the container such that the stirring motion imposed on the chamber is also imposed on the measuring module.

11. Measuring device according to claim 1, wherein the support for the measuring module is separated structurally from the chamber such that the measuring module is in relative motion with respect to the chamber when said chamber is in a stirring motion.

12. Measuring device according to claim 1, wherein the chamber has a window that is arranged with respect to the support such that the backscattered light rays and the emission light rays are capable of passing through this window during the measuring phase.

13. Process that is designed to measure the properties of a complex medium, including reversible aggregation phenomenon, by an analysis of the variation in the light that is backscattered and/or transmitted by the complex medium during a measuring phase after a preliminary stirring stage, with this complex medium comprising aggregates and being contained in a container extending in a longitudinal direction, with the process comprising the follow successive stages:
   accommodating and supporting the container with the chamber;
   holding the container in a stationary or essentially stationary position with respect to the chamber;
   emitting emission light rays with an optoelectronic unit to illuminate the complex medium and to receive light rays that are backscattered and/or transmitted by said complex medium;
   wherein the preliminary stirring stage of the container consists in:
   using a stirring element being located exterior to said holder, putting the chamber into a stirring motion comprising at least one back-and-forth movement according to a directional vector extending in a significant proportion in the longitudinal direction, with a stirring frequency which causes shear stresses in the complex medium bringing about the destruction of the aggregates of said complex medium when said container is accommodated and supported by the chamber,
   wherein the preliminary stirring stage consists in putting the chamber and the container into a stirring motion comprising at least one back-and-forth movement according to a circular translational movement around an axis of rotation, and wherein the back-and-forth movement around the axis of rotation is essentially between 10° and 90°.

14. Process according to claim 13, wherein the preliminary stirring stage consists in putting the chamber and the container into a stirring motion comprising at least one back-and-forth movement according to a unidirectional translational movement.

15. Process according to claim 13, wherein the preliminary stirring stage consists in putting the chamber and the container into a stirring motion comprising at least one back-and-forth movement in a rotation around an axis of rotation.

16. Process according to claim 13, wherein the axis of rotation is positioned at a distance that is essentially between 50 and 200 millimeters from the center of gravity of the chamber.

17. Process according to claim 13, wherein the container is held by an O-ring seal that covers a portion of the inside surface of the chamber.

18. Process according to claim 13, wherein the container is held by a clamp or a stop part that may or may not be deformable.

19. Process according to claim 13, wherein during the measuring phase:
a light source emits the emission light rays in the direction of said complex medium to illuminate said complex medium,
an optical detector receives the light rays that are backscattered and/or transmitted by said complex medium in response to the illumination of said complex medium.

20. Process according to claim 19, wherein the light source emits monochromatic radiation.

21. Process according to claim 13, wherein the a support for the measuring module is combined structurally and functionally with the chamber of the container such that the stirring motion imposed on the chamber is also imposed on the measuring module.

22. Process according to claim 13, wherein the support means of the measuring module are separated structurally from the chamber such that the support is in relative motion with respect to the chamber when said chamber is in a stirring motion.

23. Process according to claim 13, wherein the chamber has a window that is arranged with respect to the support of the measuring module such that the emission light rays and the backscattered light rays pass through this window during the measuring phase.

24. Process according to claim 13, wherein the measuring module transmits data collected during the measuring phase to an analysis unit that may or may not be structurally separate.

25. Process according to claim 24, wherein the analysis unit uses the data collected for calculating the sedimentation time of said complex medium after the measuring phase.

* * * * *